United States Patent [19]

Kuen et al.

[11] Patent Number: 5,386,595
[45] Date of Patent: Feb. 7, 1995

[54] GARMENT ATTACHMENT SYSTEM

[75] Inventors: David A. Kuen, Neenah; Alan F. Schleinz, Appleton, both of Wis.

[73] Assignee: Kimberly-Clark, Neenan, Wis.

[21] Appl. No.: 275,936

[22] Filed: Jul. 15, 1994

Related U.S. Application Data

[63] Continuation of Ser. No. 998,496, Dec. 30, 1992, abandoned.

[51] Int. Cl.6 .................. A41D 13/04; A61F 13/15
[52] U.S. Cl. ................................. 2/400; 2/402; 2/111; 24/442; 604/387; 604/391
[58] Field of Search ............... 2/400, 401, 402, 403, 2/404, 405, 406, 407, 408, 111; 128/287, 284, 289, 288; 604/391, 392, 385, 385 A, 385 R:397, 387; 24/204, 447, 444, 442, 446, 450, 306

[56] References Cited

U.S. PATENT DOCUMENTS

| | | | |
|---|---|---|---|
| 1,245,655 | 11/1917 | Allen . | |
| 1,494,044 | 5/1924 | Ward et al. . | |
| 2,516,951 | 4/1947 | Brink | 128/287 |
| 2,548,162 | 4/1951 | Karels | 128/284 |
| 2,564,094 | 5/1951 | Brandl | 128/284 |
| 2,566,139 | 5/1951 | Ostrovsky et al. | 128/284 |
| 2,827,052 | 3/1958 | Goodman et al. | 128/284 |
| 3,081,772 | 3/1963 | Brooks et al. | 128/287 |
| 3,110,312 | 11/1963 | Wirth | 128/287 |
| 3,141,461 | 7/1964 | Farris | 128/284 |
| 3,150,664 | 9/1964 | Noel | 128/287 |
| 3,196,511 | 7/1965 | Kintner | 24/204 |
| 3,359,980 | 12/1967 | Rosenblatt | 128/284 |
| 3,441,024 | 4/1969 | Ralph | 128/287 |
| 3,441,025 | 4/1969 | Ralph | 128/289 |
| 3,452,753 | 7/1969 | Sanford | 128/287 |
| 3,455,303 | 7/1969 | Wilson | 128/289 |
| 3,460,535 | 8/1969 | Behna | 128/288 |
| 3,530,859 | 9/1970 | Heimowitz | 128/284 |
| 3,618,608 | 11/1971 | Brink | 128/287 |
| 3,653,381 | 4/1972 | Warnken | 128/284 |
| 3,728,191 | 4/1973 | Wierzba et al. | 156/265 |
| 3,882,871 | 5/1975 | Taniguchi | 128/287 |
| 3,955,575 | 5/1976 | Okuda | 128/284 |
| 4,051,854 | 10/1977 | Aaron | 128/284 |
| 4,145,763 | 3/1979 | Abrams et al. | 2/403 |
| 4,171,239 | 10/1979 | Hirsch et al. | 156/461 |
| 4,241,462 | 12/1980 | Tagawa et al. | 2/406 |
| 4,259,957 | 4/1981 | Sonenstein et al. | 128/287 |
| 4,299,223 | 11/1981 | Cronkrite | 128/287 |
| 4,315,508 | 2/1982 | Bolick | 128/289 |
| 4,338,938 | 7/1982 | Seavitt | 128/284 |
| 4,340,563 | 7/1982 | Appel et al. | 264/518 |
| 4,388,075 | 6/1983 | Mesek et al. | 604/385 |
| 4,402,690 | 9/1983 | Redfern | 604/391 |
| 4,405,297 | 9/1983 | Appel et al. | 425/72 S |
| 4,410,327 | 10/1983 | Baggaley | 604/391 |

(List continued on next page.)

FOREIGN PATENT DOCUMENTS 672690  7/1960  Canada .

(List continued on next page.)

OTHER PUBLICATIONS

Gershman, Maurice, "Self Adhering Nylon Tapes," The J.A.M.A., vol. 168, No. 7, p. 930 (Oct. 1958).

Primary Examiner—Jeanette E. Chapman
Attorney, Agent, or Firm—Thomas M. Gage

[57] ABSTRACT

A garment and attachment system of the present invention include a pair of first attachment pads attached to a first waist section of a garment shell. Each first attachment pad has a primary axis directed generally toward the nearest corner of the garment shell and forming an angle of from 25 to 45 degrees with the transverse axis of the garment shell. At least one second attachment pad is attached to a second waist section of the garment shell. A pair of strap members each have forward and rearward end portions with fasteners attached thereto. The fasteners are releasably engageable with the attachment pads. In particular embodiments, the attachment pads are formed of a loop material having a predetermined loop tip orientation.

9 Claims, 7 Drawing Sheets

U.S. PATENT DOCUMENTS

| | | | |
|---|---|---|---|
| 4,445,242 | 5/1984 | Bowen | 5/484 |
| 4,475,912 | 10/1984 | Coates | 604/385 |
| 4,516,975 | 5/1985 | Mitchell | 604/385 A |
| 4,568,342 | 2/1986 | Davis | 604/391 |
| 4,578,072 | 3/1986 | Lancaster | 604/385 A |
| 4,578,073 | 3/1986 | Dysart et al. | 604/397 |
| 4,589,878 | 5/1986 | Mitrani | 604/392 |
| 4,592,118 | 6/1986 | DeWoskin | 24/444 |
| 4,596,568 | 6/1986 | Flug | 604/369 |
| 4,597,760 | 7/1986 | Buell | 604/397 |
| 4,597,761 | 7/1986 | Buell | 604/397 |
| 4,608,115 | 8/1986 | Schroth et al. | 156/519 |
| 4,610,680 | 9/1986 | LaFleur | 604/385 A |
| 4,610,682 | 9/1986 | Kopp | 604/385 R |
| 4,615,695 | 10/1986 | Cooper | 604/385 A |
| 4,617,022 | 10/1986 | Pigneul et al. | 604/391 |
| 4,623,339 | 11/1986 | Ciraldo et al. | 604/359 |
| 4,630,320 | 12/1986 | Van Gompel | 2/406 |
| 4,641,381 | 2/1987 | Heran et al. | 2/400 |
| 4,662,037 | 5/1987 | Provost et al. | 24/447 |
| 4,663,220 | 5/1987 | Wisneski et al. | 428/221 |
| 4,670,012 | 6/1987 | Johnson | 604/390 |
| 4,680,030 | 7/1987 | Coates et al. | 128/391 |
| 4,681,581 | 7/1987 | Coates | 604/391 |
| 4,704,117 | 11/1987 | Mitchell | 604/391 |
| 4,710,414 | 12/1987 | Northrup et al. | 428/43 |
| 4,728,326 | 3/1988 | Gilles | 604/391 |
| 4,745,926 | 5/1988 | Hlusko | 128/134 |
| 4,753,649 | 6/1988 | Pazdernik | 604/389 |
| 4,761,318 | 8/1988 | Ott et al. | 428/85 |
| 4,770,917 | 9/1988 | Tochacek et al. | 428/95 |
| 4,773,906 | 9/1988 | Krushel | 604/391 |
| 4,776,068 | 10/1988 | Smirlock et al. | 24/442 |
| 4,781,966 | 11/1988 | Taylor | 428/152 |
| 4,794,028 | 12/1988 | Fischer | 428/100 |
| 4,798,603 | 1/1989 | Meyer et al. | 604/378 |
| 4,801,298 | 1/1989 | Sorenson et al. | 604/384 |
| 4,834,742 | 5/1989 | Wilson et al. | 604/389 |
| 4,835,795 | 6/1989 | Lonon | 2/408 |
| 4,846,815 | 7/1989 | Scripps | 604/391 |
| 4,847,134 | 7/1989 | Fahrenkrug et al. | 428/138 |
| 4,854,136 | 8/1989 | Coslovi et al. | 66/191 |
| 4,869,724 | 9/1989 | Scripps | 604/389 |
| 4,870,725 | 10/1989 | Dubowik | 24/442 |
| 4,884,713 | 12/1989 | Handler | 220/23.4 |
| 4,886,512 | 12/1989 | Damico et al. | 609/385.2 |
| 4,887,338 | 12/1989 | Handler | 24/306 |
| 4,887,339 | 12/1989 | Bellanger | 24/575 |
| 4,891,868 | 1/1990 | Watanabe | 24/691 |
| 4,894,060 | 1/1990 | Nestegard | 604/391 |
| 4,904,249 | 2/1990 | Miller et al. | 604/338 X |
| 4,908,025 | 3/1990 | Ketchum, Jr. | 604/327 |
| 4,909,802 | 3/1990 | Ahr et al. | 604/385.1 |
| 4,909,879 | 3/1990 | Ball | 156/164 |
| 4,932,950 | 6/1990 | Johnson | 604/392 |
| 4,936,840 | 6/1990 | Proxmire | 604/385.2 |
| 4,937,887 | 7/1990 | Schreiner | 2/402 |
| 4,938,754 | 7/1990 | Mesek | 604/385.2 |
| 4,963,140 | 10/1990 | Robertson et al. | 604/389 |
| 4,964,860 | 10/1990 | Gipson et al. | 604/391 |
| 4,973,326 | 11/1990 | Wood et al. | 604/391 |
| 4,981,480 | 1/1991 | Gaudet et al. | 604/386 |
| 4,988,346 | 1/1991 | Pfefferkorn | 604/389 |
| 4,994,054 | 2/1991 | Pigneul et al. | 604/391 |
| 5,019,073 | 5/1991 | Roessler et al. | 604/391 |
| 5,021,111 | 6/1991 | Swenson | 156/264 |
| 5,026,450 | 6/1991 | Cucuzza et al. | 156/244.11 |
| 5,032,122 | 7/1991 | Noel et al. | 604/391 |
| 5,049,145 | 9/1991 | Flug | 24/442 |
| 5,100,399 | 3/1992 | Janson et al. | 604/386 |
| 5,125,246 | 6/1992 | Shytles | 66/193 |
| 5,193,225 | 3/1993 | Karami et al. | 2/311 |
| 5,209,743 | 5/1993 | Hardison | 604/391 |
| 5,318,555 | 6/1994 | Siebers et al. | 604/390 |

FOREIGN PATENT DOCUMENTS

| | | | |
|---|---|---|---|
| 013463 | 1/1979 | European Pat. Off. | 128/463 |
| 0013463A1 | 7/1980 | European Pat. Off. | |
| 0013463 | 7/1980 | European Pat. Off. | |
| 0120790A1 | 10/1984 | European Pat. Off. | |
| 0233364A2 | 8/1987 | European Pat. Off. | |
| 0276890A2 | 8/1988 | European Pat. Off. | |
| 0276970A2 | 8/1988 | European Pat. Off. | |
| 0278866A1 | 8/1988 | European Pat. Off. | |
| 0287388A2 | 10/1988 | European Pat. Off. | |
| 0319249A1 | 6/1989 | European Pat. Off. | |
| 0321232A1 | 6/1989 | European Pat. Off. | |
| 0321234A1 | 6/1989 | European Pat. Off. | |
| 0330793A1 | 9/1989 | European Pat. Off. | |
| 0345014A3 | 12/1989 | European Pat. Off. | |
| 0374730A2 | 6/1990 | European Pat. Off. | |
| 2335165 | 8/1977 | France. | |
| 2586558A1 | 3/1987 | France. | |
| 63-2708 | 1/1988 | Japan. | |
| 493819 | 10/1938 | United Kingdom. | |
| 1428572 | 3/1976 | United Kingdom. | |
| 1430747 | 4/1976 | United Kingdom. | |
| 2074011A | 10/1981 | United Kingdom. | |
| 2144637A | 3/1985 | United Kingdom. | |
| 2200530A | 8/1988 | United Kingdom. | |
| 2201893A | 9/1988 | United Kingdom. | |
| 2233876A | 1/1991 | United Kingdom. | |
| 2242612A | 10/1991 | United Kingdom. | |
| 2248379A | 4/1992 | United Kingdom. | |
| 1095397 | 12/1967 | WIPO | A41B 13/02 |
| WO85/03205 | 8/1985 | WIPO. | |
| WO88/06014 | 8/1988 | WIPO. | |
| WO88/07335 | 10/1988 | WIPO. | |
| WO91/03220 | 3/1991 | WIPO. | |
| WO91/08725 | 6/1991 | WIPO. | |
| WO92/10957 | 7/1992 | WIPO. | |

GARMENT ATTACHMENT SYSTEM

This is a continuation of copending application Ser. No. 07/998,496 filed on Dec. 30, 1992, now abandoned

BACKGROUND OF THE INVENTION

The present invention relates generally to the field of garments with attachment systems. More particularly, the invention pertains to an improved attachment system for maintaining a garment in the crotch region of a wearer.

The present invention is intended for use with a wide variety of garments that are to be worn in the crotch region. Such garments may include disposable absorbent articles, underwear, bathing suits, athletic supporters, prosthetics, or other personal care or health care garments. With particular reference to disposable absorbent articles, these articles include such things as incontinence garments, disposable diapers, briefs, training pants, or the like. Disposable articles for the absorption and containment of urine and other body exudates are generally unitary, preshaped or prefolded, and are comprised of a fluid pervious bodyside liner, a fluid impervious backing sheet, and an absorbent material disposed between the bodyside liner and the backing sheet. They generally include some type of attachment system for securing the garment to the body of the wearer.

The types of attachment systems used on disposable absorbent articles has varied widely. In some systems, the front and back waist sections are directly attached to one another with a fastener. In other attachment systems, the front and back waist sections are connected via a strap or belt. For example, the garment suspension system described in U.S. Pat. No. 4,315,508 to Bolick includes two elastic straps that are provided with buttons or other fastening means. The garment described in U.S. Pat. No. 4,617,022 to Pigneul et al. includes a removable belt that may be attached to the garment with hook-and-loop type fasteners.

There are several important characteristics for garments that are intended to be maintained in the crotch region by an attachment system. Initially, the garment needs to be somewhat adjustable to accommodate at least some range of body sizes. Secondly, the garment needs to be properly oriented on the wearer. And finally, the attachment system needs to remain securely fastened so that the garment remains adjusted for the particular size of the wearer and oriented properly on the wearer. As can be appreciated, these characteristics may be especially important for disposable absorbent articles, where a poorly fitting garment or an improperly adjusted garment can result in leakage.

Heretofore, garments and the attachment systems therefor have not satisfactorily addressed all of these characteristics in a single product. For example, present attachment systems may provide adjustability but sacrifice the proper orientation on the body. Others may provide a mechanism for achieving a proper orientation but lack adjustability. Still other attachment systems that employ hook-and-loop fasteners often do not promote secure engagement of the fasteners.

SUMMARY OF THE INVENTION

In response to the discussed drawbacks and problems encountered in the past, a new garment with an attachment system has been discovered. In one aspect, a garment according to this invention includes a garment shell having a first end, an opposite second end and longitudinal sides extending between the ends. Corners of the shell are formed at the intersections of the ends and the sides. The garment shell, which defines a longitudinal axis and a transverse axis, also has a first waist section adjacent the first end and a second waist section adjacent the second end. A pair of first attachment pads are attached to the first waist section. Each of the first attachment pads has a primary axis that is directed generally toward the nearest corner of the garment shell and forms an angle of from 25 to 45 degrees with the transverse axis of the garment shell. At least one second attachment pad is attached to the second waist section. The garment also includes a pair of strap members, with each strap member having a forward end portion and a rearward end portion. A fastener is attached to each of the forward and rearward end portions, with those attached to the forward end portions being releasably engageable with the first attachment pads, and those attached to the rearward end portions being releasably engageable with the second attachment pad. This aspect of the invention provides a garment which will be adjustable and properly oriented on the wearer.

In particular embodiments described hereinafter, the first and second attachment pads are formed of a loop material having specific loop tip orientations and the fasteners are formed of a hook material. The loop tip orientation of the first attachment pads, for example, is desirably directed toward the first end and is perpendicular to the primary axis that is directed generally toward the nearest corner. This aspect provides an attachment system with secure attachment of the hook-and-loop fasteners.

In other embodiments, the garment includes a pair of second attachment pads attached to the second waist section. Each second attachment pad has a primary axis directed generally toward the nearest corner of the garment shell and forming an angle of from 15 to 45 degrees with the transverse axis of the garment shell. Desirably, the angle formed between the primary axis of each second attachment pad and the transverse axis of the garment shell is less than the angle formed between the primary axis of each first attachment pad and the transverse axis of the garment shell. The shape and angular positioning of the attachment pads prompt the wearer to attach the strap members in a manner that properly orients the garment on the wearer. As more fully explained hereinafter, attaching the strap members at the angles of the attachment pads causes the strap members to be positioned toward the hips of the wearer.

In another aspect of the invention, a pair of first attachment pads are attached to the first waist section, with each of the first attachment pads having a longitudinal axis directed generally toward the nearest corner of the garment shell and forming an angle of from 25 to 45 degrees with the transverse axis of the garment shell. Each of the first attachment pads is formed of a loop material having a loop tip orientation perpendicular to the longitudinal axis of each first attachment pad and directed toward the first end. A pair of second attachment pads are attached to the second waist section, with each of the second attachment pads being formed of a loop material having a loop tip orientation parallel to the longitudinal axis of the garment shell and directed toward the first end. In particular embodiments, the first and second attachment pads are attached to the garment shell with a plurality of parallel lines of adhesive.

In a further embodiment of the invention, a garment includes a garment shell having a first end, a second end, longitudinal sides extending between the ends, corners at the intersections of the ends and the sides, a first waist section adjacent the first end, and a second waist section adjacent the second end. The garment shell defines a longitudinal axis and a transverse axis. A pair of first hook patches are attached to the first waist section with each first hook patch having a longitudinal axis directed generally toward the nearest corner and forming an angle of from 25 to 45 degrees with the transverse axis of the garment shell. A pair of second hook patches are attached to the second waist section. A pair of strap members, each having opposite faces with at least one face formed of a loop material, are releasably engageable with the first and second hook patches.

In a still further embodiment of the invention, a garment includes a garment shell having a first end, a second end, longitudinal sides extending between the ends, a first waist section adjacent the first end, and a second waist section adjacent the second end. The garment shell, which defines a longitudinal axis and a transverse axis, includes a substantially liquid permeable bodyside liner, an absorbent core, and a substantially liquid impermeable backing sheet attached to the bodyside liner and sandwiching the absorbent core therebetween. At least the bodyside liner and the backing sheet define a pair of first slots formed in the first waist section and a pair of second slots formed in the second waist section. Each first slot has a longitudinal axis intersecting the first end and the nearest longitudinal side, and forming an angle of from 25 to 45 degrees with the longitudinal axis of the garment shell. Similarly, each second slot has a longitudinal axis intersecting the second end and the nearest longitudinal side, and forming an angle of from 15 to 45 degrees with the longitudinal axis of the garment shell. The garment also includes a pair of strap members, each having a looped face formed of a loop material, an opposite face, a forward end portion and a rearward end portion. A hook patch formed of a hook material is attached to each of the forward and rearward end portions and releasably engageable with the loop material of the looped face.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DETAILED DESCRIPTION OF THE PREFERRED EMBODIMENTS

Figure 1:
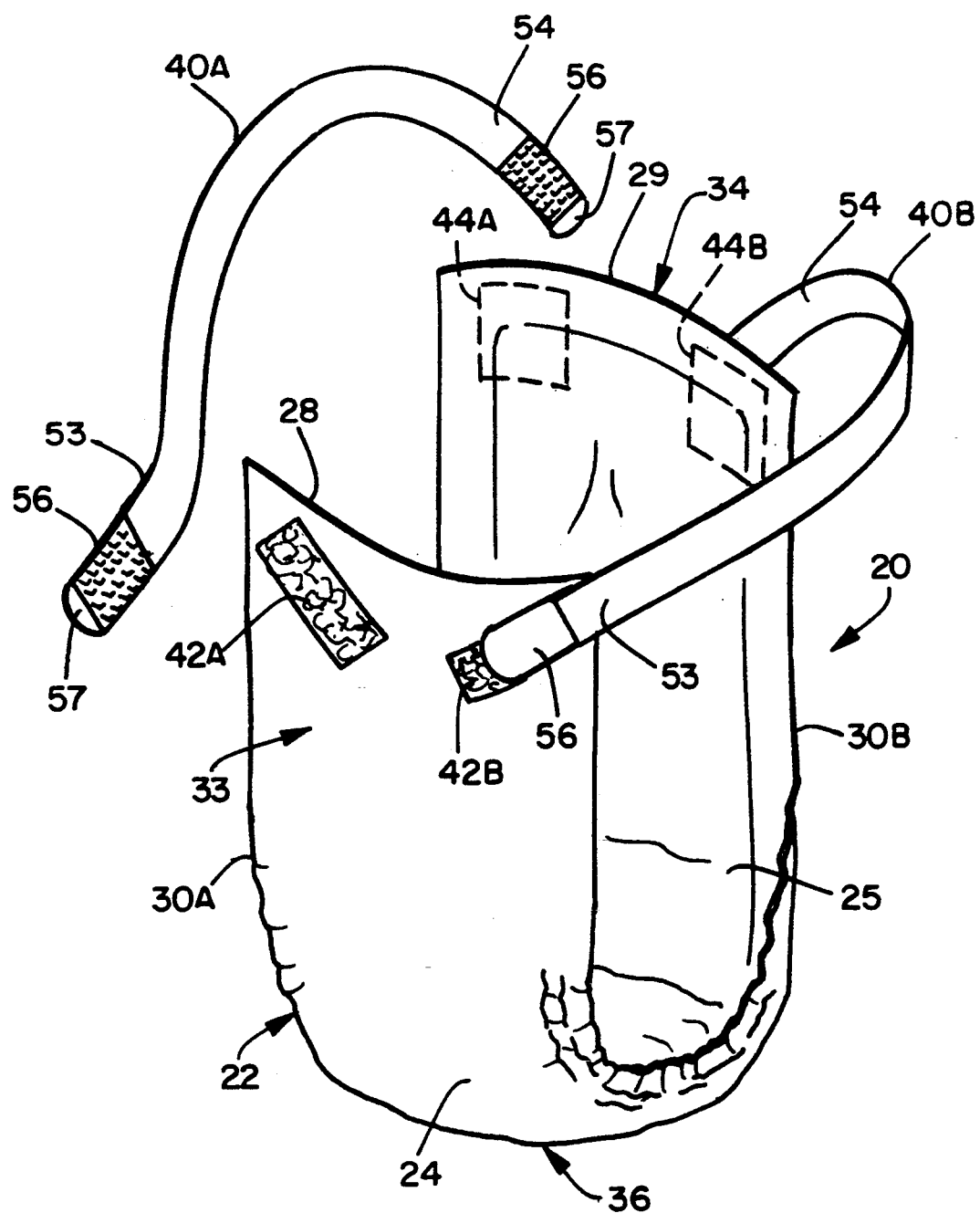
FIG. 1 is a perspective view of a disposable absorbent garment according to the present invention.
Figure 2:
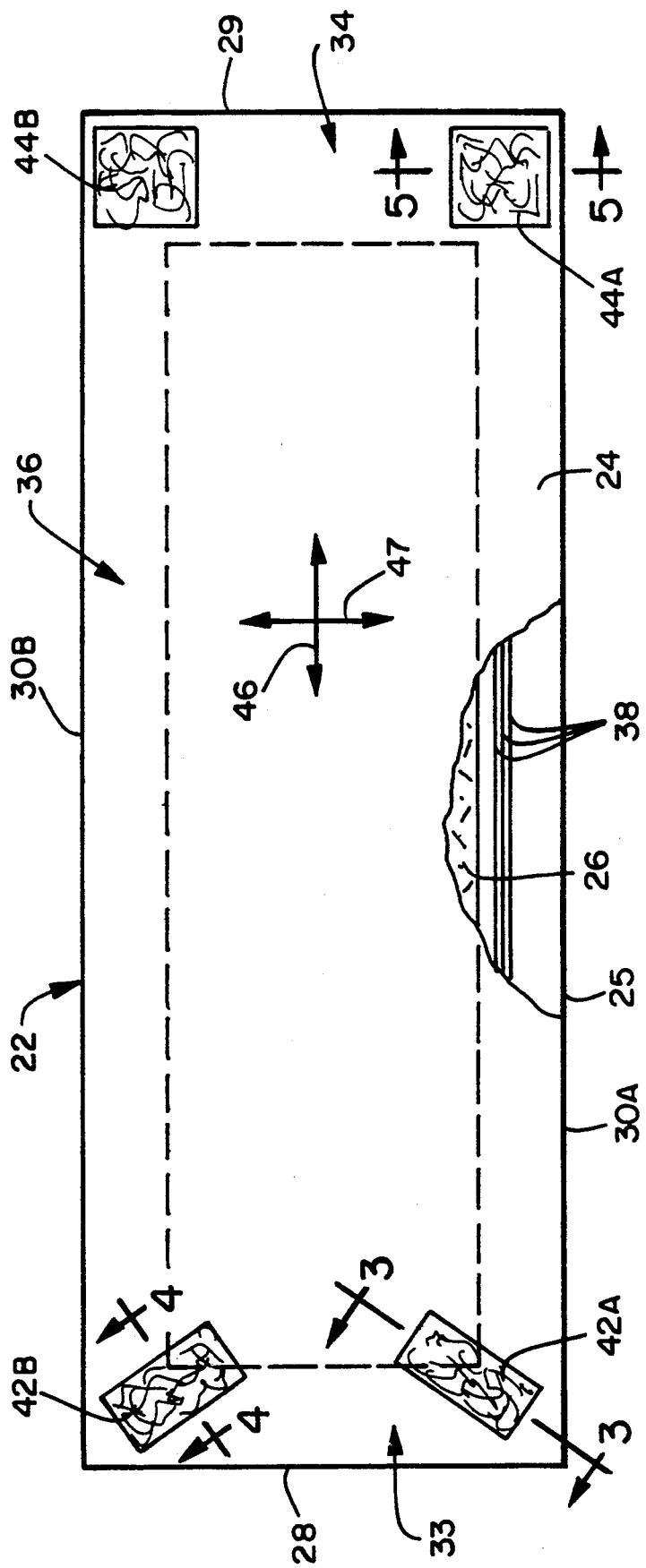
FIG. 2 is a plan view of a garment shell of the disposable absorbent garment shown in FIG. 1, with portions broken away for the purposes of illustration.

With reference to FIGS. 1 and 2, a disposable absorbent garment 20 formed according to the present invention is shown for purposes of illustration as an incontinence product for adults. The invention may also be embodied in other types of garments, such as other disposable absorbent articles, underwear, bathing suits, athletic supporters, prosthetics, or other personal care or health care garments.

The disposable absorbent garment 20 generally includes a garment shell 22 that is adapted to be used in conjunction with an attachment system. As shown, the shell 22 includes a substantially liquid impermeable backing sheet 24, a substantially liquid permeable bodyside liner 25, and an absorbent core 26 sandwiched between the backing sheet and the bodyside liner. The backing sheet 24 and bodyside liner 25 are preferably longer and wider than the absorbent core 26, so that the peripheries of the backing sheet and bodyside liner form margins which may be sealed together using ultrasonic bonds, adhesives, or other suitable means. The absorbent core 26 may be attached to the backing sheet 24 and/or the bodyside liner 25 using ultrasonic bonds, adhesives, or other suitable means. The garment 20 may also include additional components to assist in the acquisition, distribution and storage of waste material. For example, the garment 20 may include a transport layer, such as described in U.S. Pat. No. 4,798,603 to Meyer et al., which is incorporated herein by reference to the extent that it is consistent herewith.

The garment shell 22 as shown is generally rectangular with a first or front end 28, an opposite second or back end 29, and longitudinal sides 30A and 30B extending between the front and back ends. Corners of the garment shell 22 are formed at the intersections of the ends 28 and 29 and the longitudinal sides 30A and 30B. The garment shell 22 also includes a first or front waist section 33 adjacent the front end 28 and an opposite second or back waist section 34 adjacent the back end 29. A crotch section 36 is located intermediate the front and back waist sections 33 and 34. When the garment shell 22 is placed on a wearer, the front waist section 33 is generally the portion of the garment located forward of the crotch region of the wearer, and the back waist section is generally the portion of the garment located rearward of the crotch region of the wearer. The garment shell 22 may be rectangular with a length in the range of from about 10 to about 34 inches (ca. 25–86 cm.), and a width in the range of from about 2 to about 22 inches (ca. 5–56 cm.), Of course, the garment shell 22 may optionally be T-shaped, I-shaped, hourglass-shaped, or irregularly-shaped.

The shell 22 may include elastic strands or ribbons 38 (FIG. 2) longitudinally orientated along each side margin of the garment 20 and attached in a stretched condition to the backing sheet 24, the liner 25, or both. The elastic strands 38 are located in the crotch section 36 and extend toward or into the front and back waist sections 33 and 34. The elastic strands 38 may assist in holding the shell 22 against the body of the wearer or forming seals or gaskets about the leg of the wearer.

The attachment system in this embodiment of the invention includes a pair of strap members 40A and 40B, a pair of first or front attachment pads 42A and 42B, and a pair of second or back attachment pads 44A and 44B. The front and back attachment pads 42 and 44, which comprise the loop component of a hook-and-loop fastening system, may be formed of the same loop material. The term loop material is intended to mean a fabric having a base portion and a plurality of loop members extending upwardly from at least one surface of the base portion.

Figure 3:
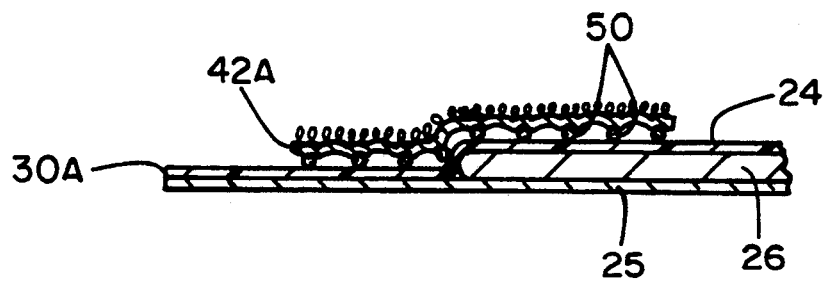
FIG. 3 is an enlarged view in section taken generally from the plane of the line 3—3 in FIG. 2.
Figure 4:
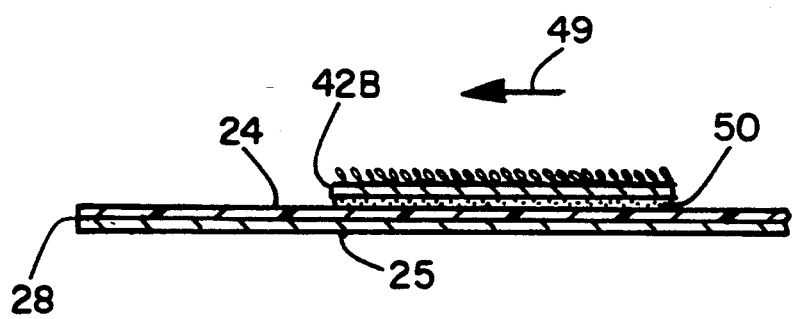
FIG. 4 is an enlarged view in section taken generally from the plane of the line 4—4 in FIG. 2.
Figure 5:
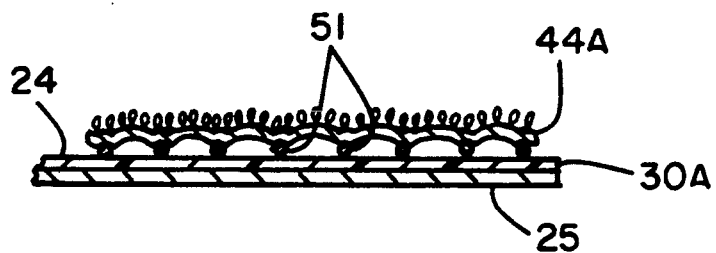
FIG. 5 is an enlarged view in section taken generally from the plane of the line 5—5 in FIG. 2.

The front and back attachment pads 42 and 44 are illustrated in enlarged and exaggerated detail in FIGS. 3-5. The loop material can comprise a material manufactured to have a raised loop construction, stabilized through napping and thermosetting so that the individual loops are erect from the fabric base. The loop material may be formed of any suitable material, such as acrylic, nylon or polyester, and may be formed by methods such as warp knitting, stitch bonding or needle punching. The attachment pads 42 and 44 can also be any suitable material having non-woven loops thereon.

In a preferred embodiment, the front and back attachment pads 42 and 44 have a two bar warp knit construction, with from 21 to 41 courses per inch (ca. 8–16 per cm.) and from 26 to 46 wales per inch (ca. 10–18 per cm.), of polyester yarn. In particular, about 15–35 percent of the yarns may be composed of yarn having about 1–30 individual filaments therein and having a yarn denier within the range of about 15–30 d (denier). In addition, about 65–85 percent of the yarns may be composed of yarn having about 1–30 individual filaments therein and having a yarn denier within the range of about 20–55 d. Also, the loops may particularly be formed with a loop height from about 2 to about 2.5 millimeters. The caliper may be from about 0.010 to about 0.040 inch (ca. 0.25–1 mm.) and the basis weight may be from about 1.0 to about 3.0 ounces per square yard (ca. 34–102 grams per square meter). One particular material which has been found suitable for the front and back attachment pads 42 and 44 is identified as No. 19902 and is available from Guilford Mills of Greensboro, N.C.

The preferred loop material will have a loop tip orientation in a single direction. As used herein, loop tip orientation refers to the general direction in which the tips of the loop members are bent. This direction, which will be in the plane of the loop material, is caused by the napping process used to make the loop material. However, the loop tip orientation may be generated by other processes as well, such as brushing, scraping, nipping, rolling, pressing, differential crepeing, combing and so forth. The loop tip orientation of a loop material can be established by selecting appropriate manufacturing processes and equipment as known in the art.

The loop tip orientation can be easily although approximately detected by rubbing the surface of a loop material and sensing the relative ease of movement in different directions. Movement in the direction of the loop tip orientation is relatively easy, whereas movement in the direction opposite the loop tip orientation is more difficult. The result can be verified by visual inspection of the loop fibers. Moreover, microscopic analysis of the loop material can also be used to more precisely determine the loop tip orientation. The individual loops comprise a fiber projecting from a particular region of the fabric base. The term fiber tip will be used to refer to the portion of the fiber furthest from the fabric base, as measured along the fiber. The loop tip orientation for a particular fiber loop is measured in relation to a line perpendicular to the fabric base and centered between the points where the fiber projects from the fabric base.

In a loop material having no loop tip orientation, the fiber tips tend to be positioned generally adjacent such perpendicular lines. In a material having a loop tip orientation, the tips of at least about 20 percent of the fibers form angles of at least about 10 degrees with such perpendicular lines, and at least about 50 percent of the fibers are oriented in substantially one direction. Desirably, the tips of at least about 30 percent of the fibers form angles of at least about 10 degrees from perpendicular; the tips of at least about 10 percent of the fibers form angles of at least about 20 degrees from perpendicular; and at least about 60 percent of the fibers are oriented in substantially one direction. The term substantially one direction is used to mean one direction or within about 35 degrees thereof, particularly within about 25 degrees thereof.

The angle from perpendicular may be measured by obtaining one or more relatively small samples of the loop material, such as about 4 to 8 centimeters in length; folding each sample along the machine direction axis of the loop material; viewing the folded edge at approximately 15X to 20X magnification using a stereomicroscope with a macro lens and back-lighted bright-field illumination; identifying individual loops formed of unbroken fibers; selecting the center of each individual loop, that is the approximate midpoint between the points where each individual loop fiber projects from the fabric base; and measuring the angle formed between a perpendicular passing through the center of the loop and a ray extending from the center of the loop to the fiber tip. Of course, the samples may have to be folded in other directions, such as along the transverse machine direction axis of the loop material, in order to identify the loop tip orientation. The preferred loop tip orientation of the front and back attachment pads 42 and 44 is discussed hereinafter.

The front attachment pads 42A and 42B are located in the front waist section 33 and attached to the surface of the backing sheet 24 that is remote from the bodyside liner 25. The pads 42A and 42B are separated from one another, positioned adjacent the opposite sides 30A and 30B, and preferably although not necessarily spaced from the front end 28 and the longitudinal sides 30A and 30B by at least about 0.25 inch (ca. 6.5 mm.).

While the size and shape of the front attachment pads 42A and 42B may vary somewhat, it has been determined that the particular attachment pads disclosed herein provide adjustability for the attachment system and at the same time promote the proper orientation of the garment 20 on the wearer. The front attachment pads 42A and 42B are preferably rectangular in shape measuring approximately 1.25 inches by 3.38 inches (ca. 3 by 9 cm.). Each front attachment pad 42 has two primary axes, the longitudinal axis and the transverse axis, which lie in the plane of the attachment pad. For pads having one long dimension, such as rectangular pads as is preferred, the term longitudinal axis is used to mean the axis parallel to the longer dimension of the attachment pad. To illustrate, the longitudinal axis of attachment pad 42A is parallel to cutting plane line 3—3 in FIG. 2, and the longitudinal axis of attachment pad 42B is perpendicular to cutting plane line 4—4 in FIG. 2. The term transverse axis is used to mean the axis perpendicular to the longitudinal axis.

To promote a proper orientation of the garment 20 on the wearer, the front attachment pads 42A and 42B are attached at specified angles in relation to the longitudinal and transverse axes of the garment shell 22, which are represented by arrows 46 and 47 respectively in FIG. 2. Specifically, each front attachment pad 42 is attached to the backing sheet 24 such that a primary axis of each front attachment pad is directed generally toward the nearest corner of the garment shell 22 and forms an angle in the range of from about 25 to about 45 degrees with the transverse axis 47 of the garment shell. Reference to a primary axis being directed generally toward the nearest corner is meant only to indicate the proper angular orientation of the primary axis with respect to the transverse axis 47; it is not intended to specify or limit the distance the primary axis may be from the corner. Most desirably, the longitudinal axis is the primary axis that is oriented the manner indicated. In that case, each front attachment pad 42A and 42B is attached to the backing sheet 24 such that the longitudinal axis of the attachment pad is directed generally toward the nearest corner of the garment shell 22 and forms an angle in the range of from about 25 to about 45 degrees with the transverse axis 47 of the garment shell. In the embodiment illustrated herein (see FIG. 2), each front attachment pad 42 is positioned such that its longitudinal axis forms an angle of about 35 degrees with the transverse axis 47 of the garment shell 22. Alternately but less desirably, each front attachment pad 42 could be attached such that its transverse axis is directed generally toward the nearest corner of the garment shell 22 and forms an angle in the range of from about 25 to about 45 degrees with the transverse axis of the garment shell (not shown).

The front attachment pads 42A and 42B are desirably attached to the backing sheet 24 with a plurality of generally parallel lines of adhesive 50 (FIGS. 3 and 4). The lines of adhesive 50 are desirably generally perpendicular to the primary axis of each front attachment pad 42A and 42B that forms the angle of from about 25 to about 45 degrees with the transverse axis 47. As shown in FIGS. 1-4, the longitudinal axis of each front attachment pad 42 forms an angle in the range of from about 25 to about 45 degrees with the transverse axis of the garment shell 22, and the lines of adhesive 50 are generally perpendicular to the longitudinal axis of each front attachment pad. The lines of adhesive 50 may have widths from about 1 to about 15 millimeters, particularly about 3 millimeters, and be spaced apart from one another by from about 1 to about 30 millimeters, particularly about 3 millimeters. As suggested schematically in FIG. 3, securing the front attachment pads 42A and 42B to the backing sheet 24 in this manner advantageously allows the loop material of the pads to form small corrugations and arch outward from the backing sheet between the lines of adhesive 50. Hook material thereby has an improved opportunity to become secured in the loops of the attachment pads 42A and 42B. Optionally, of course, the attachment pads 42A and 42B may be attached to the backing sheet 24 by ultrasonic bonds, other patterns of adhesives, or other suitable means.

The loop tip orientation of the attachment pad loop material has been found to affect performance of the attachment system. Desirably, the loop tip orientation of either front attachment pad 42A or 42B is generally perpendicular to the primary axis of the attachment pad that forms the angle of from about 25 to about 45 degrees with the transverse axis 47, and the loop tip orientation is directed toward the front end 28 of the shell 22. Desirably, the longitudinal axis of each front attachment pad 42 forms an angle in the range of from about 25 to about 45 degrees with the transverse axis of the garment shell 22, and the loop tip orientation of each front attachment pad is generally perpendicular to the longitudinal axis of each attachment pad and directed toward the front end 28 of the shell 22. This loop tip orientation is illustrated schematically in FIG. 4 in the direction of arrow 49. This particular loop tip orientation provides secure attachment of the garment 20 to the wearer. Alternately, however, the loop tip orientation of either front attachment pad 42A or 42B could be generally parallel to the longitudinal axis of the attachment pad and directed away from the corner of the garment shell 22 that is closest to the attachment pad.

The back attachment pads 44A and 44B are located in the back waist section 34 and attached to the surface of the backing sheet 24 that is remote from the bodyside liner 25. The back attachment pads 44A and 44B are spaced from one another, positioned adjacent the opposite sides 30A and 30B, and desirably although not necessarily spaced from both the second end 29 and the longitudinal sides 30A and 30B of the shell 22 by at least about 0.25 inch (ca. 6.5 mm.). The back attachment pads 44A and 44B may be formed in a wide variety of shapes and sizes. Desirably, however, each pad 44A and 44B is at least 1 inch by 1 inch (ca. 25 by 25 mm.), providing a surface area of at least about 6.25 square centimeters. For example, rectangular back attachment pads 44 measuring 1.5 inch by 2.0 inch (ca. 38 by 51 mm.), with the longer dimension of the attachment pad aligned with the transverse axis 47 of the garment shell 22, are desirable. Alternately, the back attachment pads 44 could be formed as a single pad of loop material (not shown) attached across the back waist section 34.

Like the front attachment pads 42, the back attachment pads are desirably attached to the backing sheet 24 with a plurality of generally parallel lines of adhesive 51 (FIG. 5). Here, the lines of adhesive 51 are desirably generally parallel to the longitudinal axis 46 of the garment shell 22. The lines of adhesive 51 may have widths from about 1 to about 15 millimeters, particularly about 3 millimeters, and be spaced apart from one another by from about 1 to about 30 millimeters, particularly about 3 millimeters. This manner of securing the back attachment pads 44 allows the loop material to form small corrugations and improves the opportunity for a hook material to become secured in the loop material. Optionally, ultrasonic bonds, other patterns of adhesives, or other suitable means of securing the back attachment pads 44 could be employed.

The loop tip orientation of the back attachment pads 44 is preferably oriented to provide improved securement of the garment 20 to the wearer. Desirably, the loop tip orientation of either back attachment pad 44 is generally parallel to the longitudinal axis 46 of the garment shell 22 and directed toward the opposite or front end 28 of the shell. Alternately, however, the loop tip orientation of either back attachment pad 44 could be generally parallel to the transverse axis 47 of the garment shell and directed toward the other back attachment pad.

The strap members 40A and 40B (FIG. 1) are each generally rectangular strips of material having opposite forward and rearward end portions 53 and 54. The strap members 40 are preferably formed of an elastic material, which is capable of stretching to approximately 2.8 to 3 times its relaxed length. The strap members 40 preferably have a length from about 6 inches to about 16 inches (ca. 15–41 cm.), and a width from about 0.5 inch to about 1.5 inches (ca. 1–4 cm.). For example, each strap member 40 may be 11 inches (ca. 28 cm.) long and 1 inch (ca. 2.5 cm.) wide. The cut ends of the strap members 40 may be bonded by ultrasonics, adhesives or other suitable means to prevent raveling.

Hook patches 56 are attached at each end portion 53 and 54 of each strap member 40, on the same side of the strap member. The hook patches 56 comprise a single-sided hook material and form the hook component of the hook-and-loop attachment system. The hook patches 56 may be of a variety of shapes, such as rectangular and measuring about 0.875 inch by about 1.125 inches (ca. 2.2 by 2.9 cm.). Each hook patch is attached to a strap member 40 by ultrasonic bonds, adhesives, stitches or other suitable means. As illustrated in FIG. 1, each hook patch 56 may include a free end 57 that is rounded and void of hooks. The free end 57 provides a convenient surface for grasping the hook patch to remove it from engagement with loop material. The hook patches 56 may be positioned in full face-to-face contact with the strap members 40 (not shown), or positioned such that hook patches extend past the ends of the strap members (see FIG. 1).

Suitable hook material may be molded or extruded of nylon, polypropylene or another suitable material. Desirable stiffness levels of the hook material may be obtained from polymeric materials having a flexural modulus of about 70,000-120,000 pounds per square inch (ca. $4.83 \times 10^8 - 8.27 \times 10^8$ nt/m$^2$) and a Shore hardness value within the range of about D-40 to D-80, such as D-61. The hook patches 56 desirably contain uni-directional hooks, with the machine direction of the hooks aligned with the longitudinal axis of the strap member 40, and the hooks facing toward the opposite end portion 53 or 54 of the strap member. One suitable single-sided hook material for the hook patches is available from Velcro Industries B.V., Amsterdam, Netherlands or affiliates thereof, and is identified as HTH-840 with No. 22 uni-directional hook pattern.

The shape, density and polymer composition of the hooks may be selected to obtain the desired peel and shear, force resistance values, as hereinafter described, between the hook patches 56 and the attachment pads 42 and 44. One skilled in the art would recognize, for instance, that a more aggressive hook material may comprise a material with a greater average hook height, a greater percentage of directionally-aligned hooks, or a more aggressive hook shape. As one example, the density of the hook members may be more than 50 hooks per square inch (ca. 8 per square cm.), and more particularly within the range of about 440 to about 1040 hooks per square inch (ca. 68–161 per square cm.), such as about 740 hooks per square inch (ca. 115 per square cm.). The row density may be within the range of about 20 to about 60 rows per linear inch of width (ca. 8–24 per linear cm.), such as about 40 rows per linear inch of width (ca. 16 per linear cm.). The hook members may be hook-shaped, mushroom-shaped, arrow-shaped or any other desired shape.

The "shear force" as referenced herein is determined according to ASTM Designation: D3654 82, "Standard Test Method for Holding Power of Pressure-Sensitive Tapes", which is incorporated herein by reference, and subject to the following modifications: In relation to the test, the closure is placed under an increasing load. The system being tested is a hook and loop closure system. (See 1. Scope). The apparatus should include an "INSTRON" or equivalent continuous rate of extension (CRE) tensile tester. (See 3. Apparatus). In carrying out the procedure (see 6. Procedure), test direction of the materials should be noted. The test materials are rolled five cycles (1 sq. in.), where one cycle equals once in each direction. The hook material is clamped into the upper jaw and the loop material clamped into the lower jaw of the Instron tensile tester. The engaged system (hook and loop) is pulled until failure. In performing the calculations (See 10. Calculations), the peak load is determined and recorded in grams.

The "peel force" is determined according to ASTM Designation: D1876-72, "Standard Test Methods for Peel Resistance of Adhesives (T-Peel Test)", which is incorporated herein by reference, and Subject to the following modifications: 4.1 No test panels are used; hook and loop materials are directly engaged and are not mounted on any other substrate unless specified. Test direction of the materials should be noted. No panels are used. The engaged test materials are rolled five cycles; where one cycle equals once in each direction. The hook material is clamped into the upper jaw and the loop material is clamped into the lower jaw.

To adequately attach the strap members 40, the hook patches 56 secure to the attachment pads 42 and 44 with a total peel resistance of at least about 150 gm., and more preferably at least about 400 gm. The hook patches 56 secure to the attachment pads 42 and 44 with a total shear force resistance of at least about 750 gm., such as 1000 gm., and more preferably at least about 2000 gm., such as 4000 gm. It should be readily recognized that a suitable fastening system will include a selected balance between the properties of total peel resistance and total shear force resistance. For example, a system with the lower values of peel resistance could be more suitable if the system also exhibited a higher total shear force resistance.

For purposes of the present description, the total peel resistance value corresponds to the peel force determined in accordance with ASTM D1876-72 multiplied by the transverse width of engagement between the hook material and the loop material employed in the particular fastening system. Similarly, the total shear force resistance value corresponds to the shear stress determined in accordance with ASTM D3654-82 multiplied by the area of engagement between the hook material and loop material of the fastening system.

In use, the garment shell 22 is positioned on the body of the wearer and secured in position using the attachment system. The first or front waist section 33 is located toward the front of the wearer, the second or back waist section 34 is located toward the posterior of the wearer, and the crotch section 36 is in place to receive body exudate. The wearer then engages one hook patch 56 of each strap member 40A and 40B with one of the back attachment pads 44A and 44B. After stretching or relaxing the strap members 40 to obtain the desired tension therein, the wearer next engages the opposite hook patches 56 of each strap member 40A and 40B with one of the corresponding front attachment pads 42A or 42B.

The angled orientation of the front attachment pads 42 (FIGS. 1 and 2) prompts the wearer to secure the hook patches 56 so that the strap members 40 are aligned with the longitudinal axis of the front attachment pads 42. Rectangular hook patches 56 and rectangular front attachment pads 42 are particularly desirable because the wearer is thereby prompted to align the long dimension of the hook patch with the long dimension of the attachment pad.

Aligning the strap members 40 at the angles of the attachment pads 42 and 44 causes the strap members to be positioned toward the hips of the wearer. In this position, the strap members 40 maintain the garment shell 22 snugly on the wearer and provide an upward force component that reduces the chance of the garment shell and strap members slipping downward.

The wearer can remove the strap members 40 by pulling on a portion of the strap near an attachment pad 42 or 44, or by pulling on a hook patch 56, such as at free end 57, to release the hook-and-loop engagement. The wearer may then increase or decrease the tension in the strap members 40 by moving the forward hook patches 56 more toward one or the other of the longitudinal ends of the front attachment pads 42. Thus, the relative sizes of the hook patches 56 and front attachment pads 42 provide for adjustability of the garment attachment system.

Furthermore, the engagement between the hook patches 56 and the attachment pads 42 and 44 is enhanced due to the disclosed loop tip orientation of the loop material. Particularly with regard to the front attachment pads 42, the shape and angular placement of the attachment pads prompt the wearer to align the strap members with the longitudinal axis of the attachment pads. As a result, the hooks of the hook patches 56 will engage the loops at a right angle with regard to the loop tip orientation. This provides a relatively strong releasable engagement over a wide variety of hook types. It also provides a relatively strong releasable engagement in the event the wearer mistakenly attaches the hook patches 56 to the front attachment pads 42 at an angle that is closer to parallel with the transverse axis of the garment shell 22.

Figure 6:
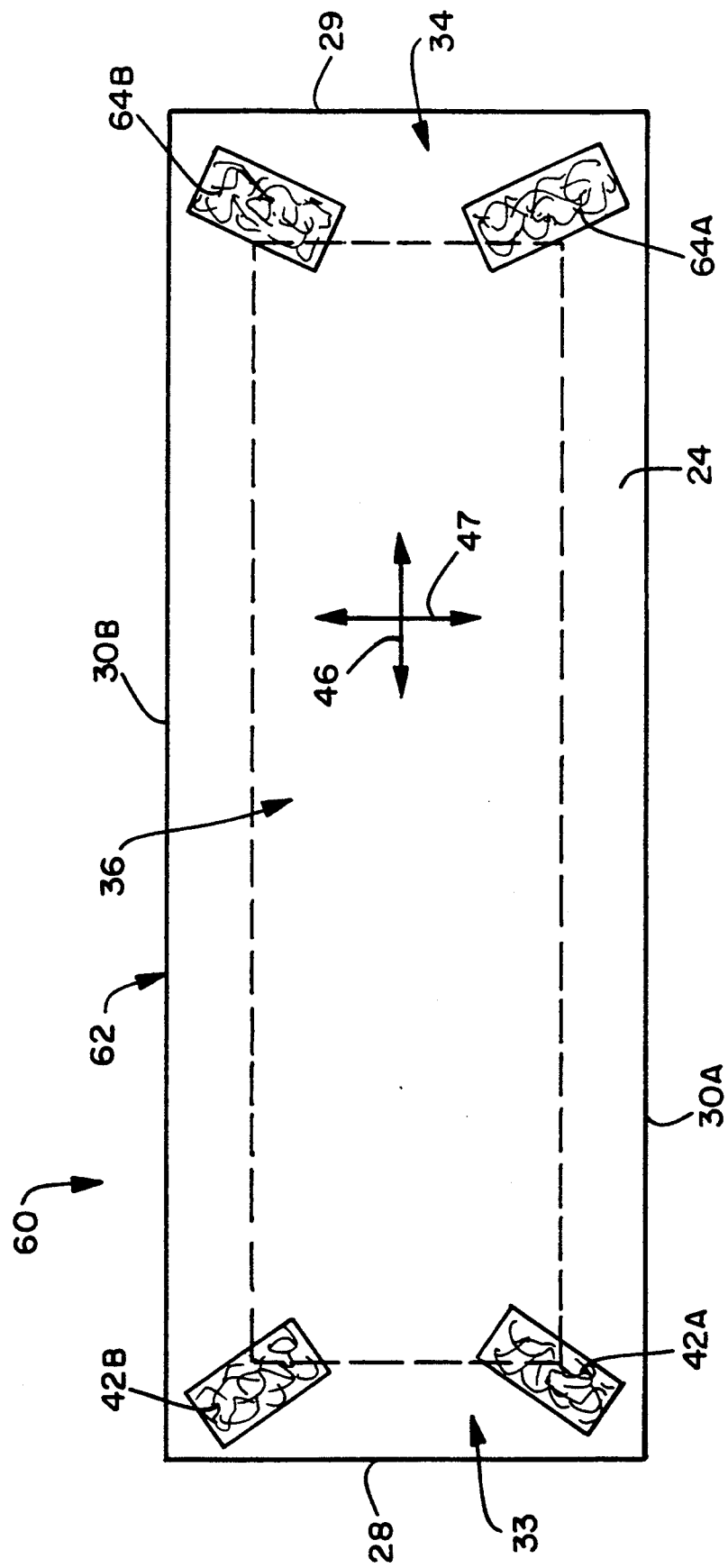
FIG. 6 is a plan view of a garment shell of an alternate embodiment of a disposable absorbent garment according to the present invention.

A second embodiment of the present invention is illustrated by garment 60 in FIG. 6, although the strap members are not shown. Components similar to those previously described have been given the same reference numeral. The garment 60 includes a shell 62 comprising a backing sheet 24, a bodyside liner 25 (now shown), and an absorbent core 26 (not shown) positioned between the backing sheet and the bodyside liner. The shell 62 is formed with a first or front end 28, an opposite second or back end 29, longitudinal sides 30A and 30B extending between the ends, corners at the intersections of the ends and the sides, a first or front waist section 33 adjacent the front end, a second or back waist section 34 adjacent the back end, and a crotch section 36 between the waist sections. The longitudinal sides of the crotch section 36 may include elastic strands 38 (not shown) between the bodyside liner 25 and the backing sheet 24 to form seals or gaskets about the leg of the wearer.

The attachment system in this embodiment of the invention includes a pair of strap members 40A and 40B (see FIG. 1), a pair of first or front attachment pads 42A and 42B, and a pair of second or back attachment pads 64A and 64B. The front and back attachment pads 42 and 64 are formed of a loop material and comprise the loop component of the hook-and-loop fastening system.

The front and back attachment pads 42 and 64 are attached to the surface of the backing sheet 24 that is remote from the bodyside liner 25. The attachment pads 42 and 64 are desirably separated from one another, positioned adjacent the opposite sides 30A and 30B, and spaced from their respective front and back ends 28 and 29 and the longitudinal sides 30A and 30B by at least about 0.25 inch (ca. 6.5 mm.). While the size and shape of the attachment pads may vary somewhat, rectangular pads measuring approximately 1.25 inches by 3.38 inches (ca. 3×9 cm.) are believed to be desirable.

Both the front and back attachment pads 42 and 64 are attached at specified angles in relation to the longitudinal and transverse axes of the garment shell 62, which axes are represented by arrows 46 and 47 respectively in FIG. 6. Desirably, each front attachment pad 42A and 42B is attached to the backing sheet 24 such that its longitudinal axis is directed generally toward the nearest corner of the garment shell 62 and forms an angle in the range of from about 25 to about 45 degrees with the transverse axis 47 of the garment shell, and each back attachment pad 64A and 64B is attached to the backing sheet such that its longitudinal axis is directed generally toward the nearest corner of the garment shell and forms an angle in the range of from about 15 to 45 degrees with the transverse axis of the garment shell. Most desirably, the back attachment pads 64 are attached such that the angle formed between the longitudinal axis of each back attachment pad and the transverse axis 47 of the garment shell 22 is less than the angle formed between the longitudinal axis of each front attachment pad 42 and the transverse axis 47. Particularly, and as illustrated in FIG. 6, each front attachment pad 42 is positioned such that its longitudinal axis forms an angle of about 35 degrees with the transverse axis 47 of the garment shell 22 and each back attachment pad 64 is positioned such that its longitudinal axis forms an angle of about 25 degrees with the transverse axis of the garment shell. Alternately, any of the attachment pads 42A, 42B, 64A or 64B could be attached such that its transverse axis is directed generally toward the nearest corner and forms an angle in the range of from about 25 to about 45 degrees (front) or from about 15 to about 45 degrees (back) with the transverse axis 47 of the garment shell 62 (not shown).

To improve engagement of the hook patches 56 to the attachment pads 42 and 64, the attachment pads are desirably attached to the backing sheet 24 with a plurality of generally parallel lines of adhesive (see FIGS. 3 and 4). The lines of adhesive are desirably generally perpendicular to the longitudinal axis of each attachment pad 42 and 64. Alternately, if the attachment pads 42A, 42B, 64A or 64B are attached such that their transverse axes are directed generally toward the nearest corner and form an angle in the range of from about 25 to about 45 degrees (front) or from about 15 to about 45 degrees (back) with the transverse axis 47 of the garment shell 62, the lines of adhesive could be generally perpendicular to the transverse axis of each attachment pad (not shown).

To further improve attachment of the hook patches 56, the loop tip orientation of either front attachment pad 42A or 42B is generally perpendicular to the longitudinal axis of the attachment pad and directed toward the front end 28 of the shell 22. Further, the loop tip orientation of either back attachment pad 64A or 64B is generally perpendicular to the longitudinal axis of the attachment pad and directed toward the back end 29 of the shell 22. Optionally, however, the loop tip orientation of any front or back attachment pad 42 or 64 could be generally parallel to the longitudinal axis of the attachment pad and directed away from the corner of the garment shell 22 that is closest to the attachment pad. Still optionally, if the attachment pads 42A, 42B, 64A or 64B are attached such that their transverse axes are directed generally toward the nearest corner and form an angle in the range of from about 25 to about 45 degrees (front) or from about 15 to about 45 degrees (back) with the transverse axis 47 of the garment shell 62, the loop tip orientation of the front attachment pads 42 could be generally perpendicular to the transverse axis of the attachment pad and directed toward the front end 28 and the loop tip orientation of the back attachment pads 64 could be generally perpendicular to the transverse axis of the attachment pad and directed toward the back end 29 (not shown).

Figure 7:
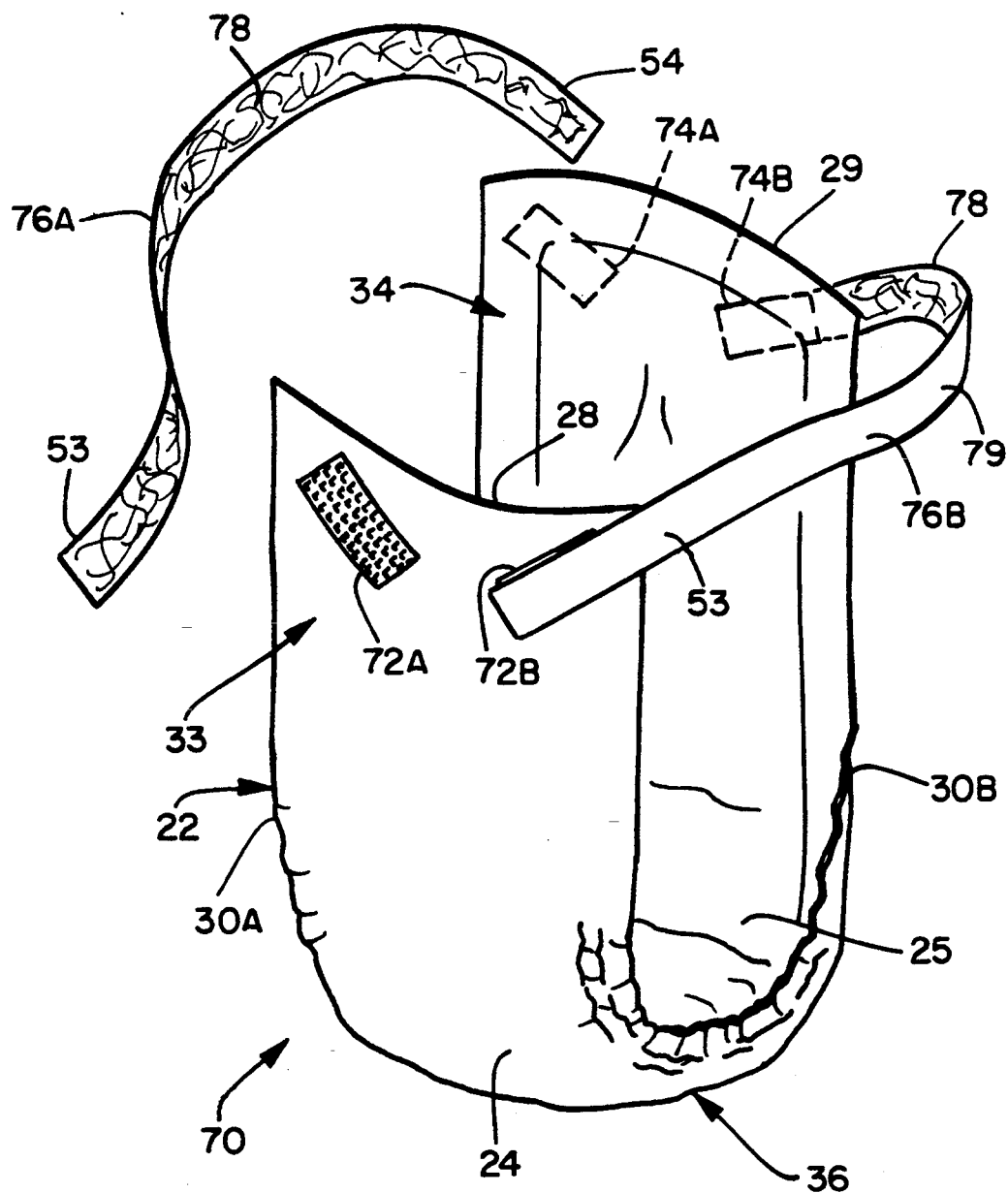
FIG. 7 is a perspective view of another alternate embodiment of a disposable absorbent garment according to the present invention.

A third embodiment of the invention is illustrated by the garment 70 in FIG. 7. The garment 70 includes a shell 22 comprising a backing sheet 24, a bodyside liner 25, and an absorbent core 26 (not shown) positioned between the backing sheet and the bodyside liner. The shell 22 is formed with a first or front end 28, an opposite second or back end 29, longitudinal sides 30A and 30B extending between the ends, corners at the intersections of the ends and the sides, a first or front waist section 33 adjacent the front end, a second or back waist section 34 adjacent the back end, and a crotch section 36 between the front and back waist sections. As with other embodiments, the sides of the crotch section 36 may include elastic strands 38 (not shown) to form seals or gaskets about the leg of the wearer.

The attachment system for the garment 70 includes two front hook patches 72A and 72B, two back hook patches 74A and 74B, and two strap members 76A and 76B. The front and back hook patches 72 and 74 comprise the hook component of a hook-and-loop fastening system, while the strap members 76 comprise the loop component of the hook-and-loop fastening system.

The front and back hook patches 72 and 74 are attached to the surface of the backing sheet 24 that is remote from the bodyside liner 25. The front hook patches 72A and 72B are located in the front waist section 33 and spaced from one another. Similarly, the back hook patches 74A and 74B are located in the back waist section 34 and separated from one another. The hook patches 72 and 74 are preferably spaced from the front and back ends 28 and 29 and longitudinal sides 30A and 30B of the garment shell 22 by at least about 0.25 inch (ca. 6.5 mm.). The size and shape of the hook patches 72 and 74 may vary somewhat, however, to promote the proper orientation and adjustability of the garment 70 on the wearer, the hook patches 72 and 74 are preferably rectangular in shape, and measure approximately 0.875 inches by 1.125 inches (ca. 2.2×2.9 cm.). The hook patches 72 and 74 may be attached to the backing sheet 24 by adhesives, ultrasonic bonds, or other suitable means.

The hook patches 72 and 74 are desirably attached at specified angles in relation to the longitudinal and transverse axes of the garment shell 22 in order to promote a proper orientation of the garment 70 on the wearer. Specifically, each front hook patch 72A and 72B is attached such that its longitudinal axis is directed generally toward the nearest corner of the garment shell 22 and forms an angle with the transverse axis of the garment shell in the range of from about 25 to about 45 degrees. Each back hook patch 74A and 74B is attached such that its longitudinal axis is directed generally toward the nearest corner of the garment shell 22 and forms an angle with the transverse axis of the garment shell in the range of from about 15 to about 45 degrees. Most desirably, the back hook patches 74A and 74B are attached such that the angle formed between their longitudinal axes and the transverse axis of the garment shell is less than the angle formed between the longitudinal axes of the front hook patches 72A and 72B and the transverse axis of the garment shell. Reference to a longitudinal axis of each hook patch 72 and 74 being directed generally toward the nearest corner is meant only to indicate the proper angular orientation of each longitudinal axis with respect to the transverse axis of the garment shell; it is not intended to specify or limit the distance the longitudinal axis may be from the corner. Alternately but less desirably, the hook patches 72 and 74 could be attached such that the transverse axis of each hook patch is directed generally toward the nearest corner of the garment shell 22 and forms an angle in the range of from about 25 to about 45 degrees (front) or from about 15 to about 45 degrees (back) with the transverse axis of the garment shell (not shown).

The strap members 76A and 76B are each generally rectangular strips of material having opposite forward and rearward end portions 53 and 54. The strap members 76 are preferably formed of an elastic material, which is capable of stretching to approximately 2.8 to 3 times its relaxed length. The strap members 76 preferably have a length from about 6 inches to about 16 inches (ca. 15–41 cm.), and a width from about 0.5 inch to about 1.5 inches (ca. 1–4 cm.). For example, each strap member 76 may be 11 inches (ca. 28 cm.) long and 1 inch (ca. 2.5 cm.) wide. The cut ends of the strap members 76 may be bonded by ultrasonics, adhesives or other suitable means to prevent raveling.

The strap members 76 have a looped face 78 and an opposite face 79. The looped face 78 of each strap member 76 is formed of a loop material, such as by attaching a loop material to an elastic strap material. The loop material may be attached only at the forward and rearward end portions 53 and 54, or along the entire length of the strap member. More preferably, the looped face 78 is separately stitched or permanently and continuously formed lock-stitched into one side of a woven or knit elastic material as it is woven or knitted. One particular material which has been found suitable as a strap member 76 is a knit material identified as S-284 and manufactured by Shelby Elastics, Incorporated, of Shelby, N. C. A knitted elastic lock pile fabric is disclosed in U.S. Pat. No. 5,125,246 to Shytles. Alternately, the strap members may have opposite faces that both comprise a loop material ( not shown ).

The garment shell 22 is positioned on the body of the wearer and secured in position using the attachment system. The rearward end portion 54 of each strap member 76 is pressed against the back hook patches 74 such that the looped face 78 of the strap member engages the hooks of the back hook patches. Thereafter, the forward end portion 53 of each strap member 76 is pressed against the front hook patches 72 such that the loops of the looped face 78 engage the hooks of the front hook patches. The angled orientation of the hook patches 72 and 74 promotes proper orientation of the garment 70 on the wearer. Also, the fit of the garment 70 may be adjusted by attaching the strap members 76 to the hook patches 72 and 74 further from or closer to the end portions 53 and 54.

Figure 8:
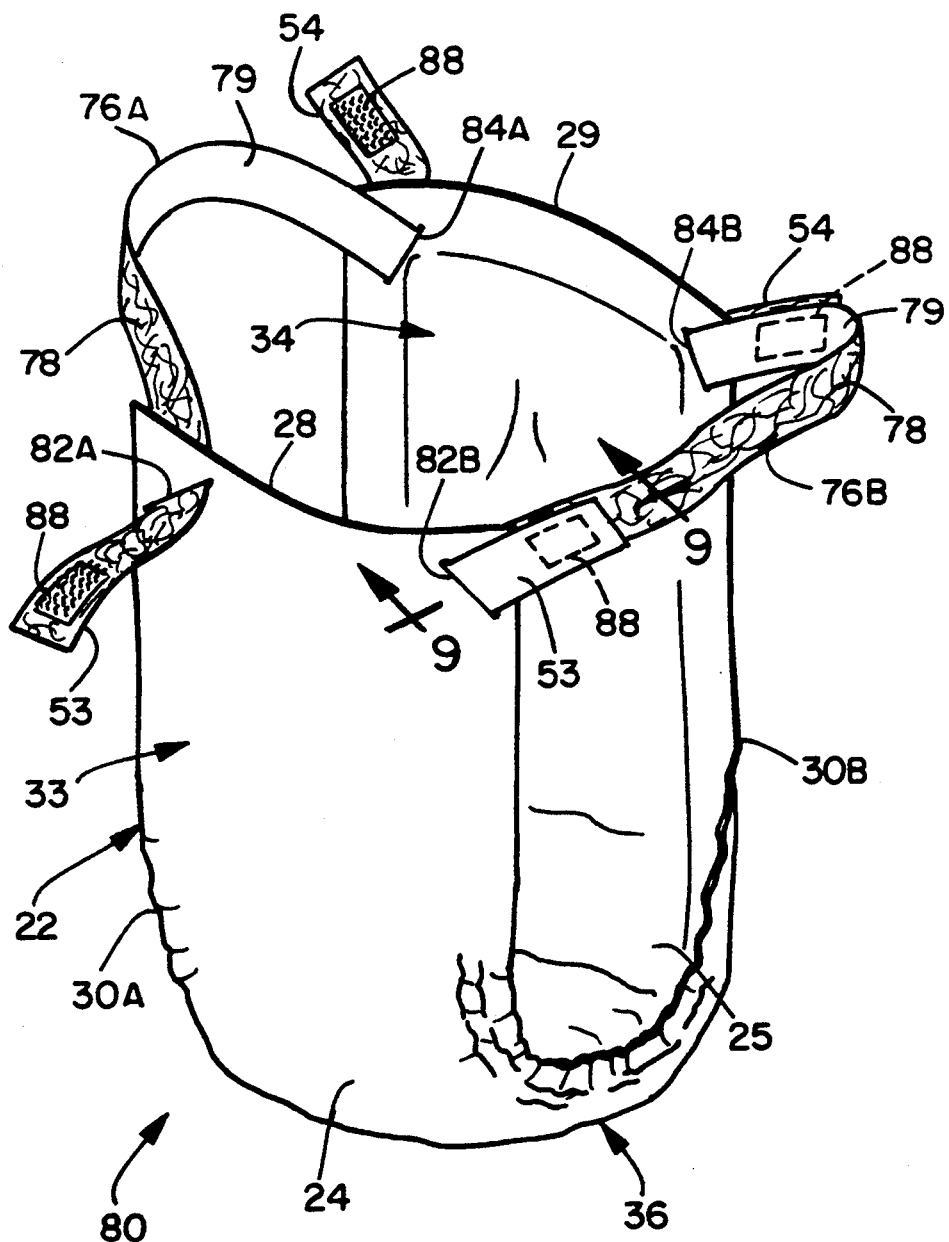
FIG. 8 is a perspective view of a still further alternate embodiment of a disposable absorbent garment according to the present invention.

A fourth embodiment of the invention is illustrated by the garment 80 in FIG. 8. The garment 80 includes a shell 22 comprising a backsheet 24, a bodyside liner 25 and an absorbent core 26 (not shown) positioned between the backing sheet and the bodyside liner. The shell 22 is formed with a first or front end 28, a second or back end 29, and longitudinal sides 30A and 30B extending between the front and back ends. The shell 22 also has a front waist section 33 adjacent the front end 28, an opposite back waist section 34 adjacent the back end 29, and a crotch section 36 therebetween. The sides of the crotch section 36 may include elastic strands 38 (not shown) to form seals or gaskets about the leg of the wearer.

The garment shell 22 is formed with a pair of first or front slots 82A and 82B and a pair of second or back slots 84A and 84B. The slots 82 and 84, which represent slits, cuts, voids or apertures, are desirably formed at the margins of the shell 22 in the backing sheet 24 and the bodyside liner 25. Optionally, the slots 82 and 84 could be formed in the shell 22 at a location that would also include the absorbent core material 26.

Each slot 82 and 84 has a longitudinal axis which lies in the plane of the garment shell 22 and extends along the long dimension of the slot. Each front slot 82A and 82B is formed such that its longitudinal axis intersects the front end 28 and the nearest longitudinal side 30A or 30B of the garment shell, and forms an angle with the longitudinal axis of the garment shell in the range of from about 25 to about 45 degrees. For instance, the front slot 82A nearest longitudinal side 30A is formed such that its longitudinal axis intersects the longitudinal side 30A and the front end 28, and the longitudinal axis forms an angle with the longitudinal axis of the garment shell 22 in the range of from about 25 to about 45 degrees. Each back slot 84A and 84B is formed such that its longitudinal axis intersects both the back end 29 and the nearest longitudinal side 30A or 30B of the garment shell 22, and forms an angle with the longitudinal axis of the garment shell in the range of from about 15 to about 45 degrees. Again, for illustration, back slot 84B is formed such that its longitudinal axis intersects both the back end 29 and the nearest longitudinal side 30B, and forms an angle with the longitudinal axis of the garment shell in the range of from about 15 to about 45 degrees.

Most desirably, the slots 82 and 84 are formed such that the angle between the longitudinal axis of each back slot 84 and the longitudinal axis of the garment shell 22 is less than the angle formed between the longitudinal axis of each front slot 82 and the longitudinal axis of the garment shell. Particularly, the front slots 82 may be formed such that their longitudinal axes form an angle of about 35 degrees with the longitudinal axis of the garment shell and the back slots 84 are formed such that their longitudinal axes form an angle of about 25 degrees with the longitudinal axis of the garment shell.

The strap members 76A and 76B are desirably rectangular strips of an elastic material, which is capable of stretching to approximately 2.8 to 3 times its relaxed length. The strap members preferably have a length from about 6 inches to about 16 inches (ca. 15–41 cm.), and a width from about 0.5 inch to about 1.5 inches (ca. 1–4 cm.). The width of the strap members 76 should be selected so that the strap members can easily pass through the slots. For example, each strap member 76 may be 11 inches (ca. 28 cm.) long and 1 inch (ca. 2.5 cm.) wide. The strap members 76 have a looped face 78 and an opposite face 79 and forward and rearward end portions 53 and 54.

Figure 9:
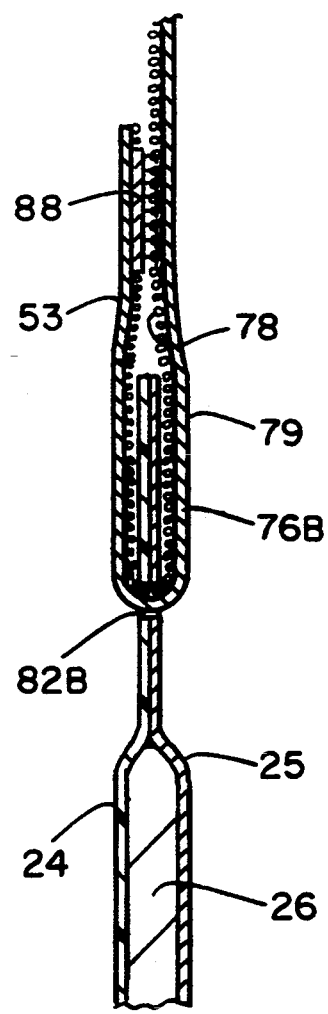
FIG. 9 is an enlarged view in section illustrating the attachment system of the disposable absorbent garment shown in FIG. 8, taken generally from the plane of the line 9—9 in FIG. 8.

With additional reference to FIG. 9, a hook patch 88 is attached at each end portion 53 and 54 of each strap member 76. The hook patches 88 comprise a single-sided hook material and form the hook component of the hook-and-loop attachment system. The hook patches 88 may be of a variety of shapes, such as rectangular and being about 0.875 inch by about 1.125 inches (ca. 2.2×2.9 cm.). Each hook patch is attached to a strap member 76 by ultrasonic bonds, adhesives, stitches or other suitable means. The slots 82 and 84 are sized to enable a forward or rearward end portion 53 or 54 of a strap member 76, including a hook patch 88 attached thereon, to pass through the slot. For example, the slots 82 and 84 may be in the form of slits having a length of about 1.12 inches (ca. 2.8 cm.).

The garment shell 22 is positioned on the body of the wearer and secured in position using the attachment system. Each rearward end portion 54 of a strap member 76 is inserted through a back slot 84 from the bodyside toward the backing sheet side. The looped face 78 of the strap member 76 is positioned away from the wearer, while the opposite face 79 is positioned toward the wearer. The rearward end portion 54 of each strap member 76 is folded back toward the central portion of the strap member and the hooks of the hook patch 88 releasably engage to the loops of the looped face 78 (see strap member 76B in FIG. 8). Similarly, the forward end portion 53 of each strap member 76 is inserted through a corresponding front slot 82A or 82B, with the looped face 78 positioned away from the wearer. The forward end portion 53 of each strap member 76 is folded back toward the center of the strap members and the hooks of the hook patches 88 are releasably attached to the loops of the looped face 78 (see also FIG. 9). Alternately of course, the strap members 76 could be inserted through the slots 82 and 84 from the backing sheet side toward the bodyside with the looped face 78 positioned toward the wearer (not shown).

The garment 80 is securely positioned on the wearer by the hook-and-loop attachment system. The angled orientation of the slots 82 and 84 promotes proper positioning of the attachment system for the garment 80. Additionally, the fit of the garment 80 may be adjusted by releasing the hook patches 88 from the looped face 78 and moving the hook patches either closer to or further from the end portions of the strap member.

A wide variety of materials may be used to construct the aforementioned components of the garments (20 in FIG. 1; 60 in FIG. 6; 70 in FIG. 7; and 80 in FIG. 8). The backing sheet 24, for example, may comprise a thin, substantially liquid impermeable web or sheet of plastic film such as polyethylene, polypropylene, polyvinyl chloride or similar material. The backing sheet material may be transparent or opaque and have an embossed or matte surface. One preferred material for the backing sheet 24 is a polyethylene film that has a nominal thickness of about 0.001 inch and a systematic matte embossed pattern, and that has been corona treated on both sides. Alternately, the backing sheet 24 may comprise a nonwoven, fibrous web which has been suitably constructed and arranged to be substantially liquid impermeable.

The bodyside liner 25 may be any soft, flexible, porous sheet which passes fluids therethrough. The bodyside liner 25 may comprise, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton. The bodyside liner 25 has a pore size that readily allows the passage therethrough of liquids, such as urine and other body exudates. The liner 25 may be selectively embossed or perforated with discrete slits or holes extending therethrough. Optionally, the web or sheet may be treated with a surfactant to aid in liquid transfer. One preferred bodyside liner material is a wettable spunbonded polypropylene having a basis weight of 0.7 ounces per square yard. Such material may be produced by the methods and apparatus described in U.S. Pat. Nos. 4,340,563 and 4,405,297 to Appel et al., which are incorporated herein by reference.

The absorbent core 26 is preferably an air-formed batt of cellulosic fibers (i.e., wood pulp fluff). One preferred type of wood pulp fluff, which is available under the trade designation CR2054 from Kimberly-Clark Corporation of Neenah, Wisconsin, is a bleached, highly absorbent sulphate wood pulp containing softwood fibers. Optionally, the absorbent core 26 could comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers.

The absorbent core 26 may also include compounds to increase its absorbency, such as an effective amount of organic or inorganic high-absorbency materials. For example, the absorbent core 26 can include 0–95 weight percent high-absorbency material. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxpropyl cellulose, polyvinyl morpholinone, polymers and copolymers of vinyl sulfonic acid, polyacrylates, polyacylamides, polyvinyl pyridine and the like. Other suitable polymers can include hydrolyzed acrylonitrile grafted starch, acrylic acid grafted starch, and isobutylene maleic anhydride copolymers, and mixtures thereof. The hydrogel polymers are preferably sufficiently cross-linked to render the materials substantially water-insoluble. Cross-linking may, for example, be by irradiation or by covalent, ionic, van der Waals, or hydrogen bonding. Suitable materials are available from various commercial vendors, such as Dow Chemical Company, Celanese Corporation, and Allied-Colloid. Typically, the high-absorbency material is capable of absorbing at least about 15 times its weight in water, and preferably is capable of absorbing more than about 25 times its weight in water.

The high-absorbency material can be distributed or otherwise incorporated into the absorbent core 26 employing various techniques. For example, the high-absorbency material can be substantially uniformly distributed among the fibers comprising the absorbent core. The materials can also be nonuniformly distributed within the absorbent core fibers to form a generally continuous gradient with either an increasing or decreasing concentration of high-absorbency material, as determined by observing the concentration moving inward from the backing sheet 24. Alternatively, the high-absorbency material can comprise a discrete layer separate from the fibrous material of the absorbent core 26, or can comprise a discrete layer integral with the absorbent core.

Absorbent core 26 may also include a tissue wrap layer to help maintain the integrity of the fibrous core. This tissue wrap typically comprises a hydrophilic cellulosic material, such as creped wadding or a high wet-strength tissue.

The elastic strands 38 may be formed of a dry-spun coalesced multifilament elastomeric thread sold under the tradename LYCRA and available from I.E. Du Pont de Nemours and Company. Alternately, the leg elastic members 33 may be formed of other typical elastics utilized in the diaper-making art, such as a thin ribbon of natural rubber. Elasticity could also be imparted to the longitudinal side sections by extruding a hot melt elastomeric adhesive between the backing sheet 24 and the bodyside liner 25. Other suitable elastic gathering means are disclosed in U.S. Pat. Nos. 4,938,754 to Mesek and 4,388,075 to Mesek et al.

The foregoing detailed description has been for the purpose of illustration. Thus, a number of modifications and changes may be made without departing from the spirit and scope of the present invention. For instance, features illustrated or described as part of one embodiment can be used on another embodiment to yield a still further embodiment. Likewise, the attachment system may be associated with garments other than the disposable absorbent garments as described herein. Therefore, the invention should not be limited by the specific embodiments described, but only by the claims.

We claim:

1. A garment comprising:
   a garment shell having opposite inner and outer surfaces, opposite first and second ends, longitudinal sides extending between the ends, corners at the intersections of the ends and the sides, a first waist section adjacent the first end, and a second waist section adjacent the second end, the garment shell defining a longitudinal axis and a transverse axis;
   a pair of first attachment pads attached to the outer surface in the first waist section and comprising a loop material, each of the first attachment pads having a longitudinal axis directed generally toward the nearest corner of the garment shell and forming an angle of from 25 to 45 degrees with the transverse axis of the garment shell, wherein each first attachment pad has a loop tip orientation that is directed toward the first end and is perpendicular to the longitudinal axis of the first attachment pad;
   a pair of second attachment pads attached to the outer surface in the second waist section and comprising a loop material, each of the second attachment pads having a longitudinal axis directed generally toward the nearest corner of the garment shell and forming an angle of from 15 to 45 degrees with the transverse axis of the garment shell, the angle formed between the longitudinal axis of each second attachment pad and the transverse axis of garment shell being less than the angle formed between the longitudinal axis of each first attachment pad and the transverse axis of the garment shell, wherein each second attachment pad has a loop tip orientation that is directed toward the second end and is perpendicular to the longitudinal axis of the second attachment pad; and a pair of strap members, each strap member having a forward end portion and a rearward end portion with a fastener comprising a hook material attached to each of the forward and rearward end portions, the fasteners being releasably engagable with the first and second attachment pads.

2. A garment comprising:

a garment shell having a first end, an opposite second end, longitudinal sides extending between the first and second ends, corners at the intersections of the ends and the sides, a first waist section adjacent the first end, a second waist section adjacent the second end, and a crotch section between the first and second waist sections, the garment shell defining a longitudinal axis and a transverse axis;

a pair of first attachment pads attached to the first waist section, each of the first attachment pads having a longitudinal axis directed generally toward the nearest corner of the garment shell and forming an angle of from 25 to 45 degrees with the transverse axis of the garment shell, each of the first attachment pads comprising a loop material that has a loop tip orientation perpendicular to the longitudinal axis of each first attachment pad and directed toward the first end;

a pair of second attachment pads attached to the second waist section, each of the second attachment pads comprising a loop material that has a loop tip orientation parallel to the longitudinal axis of the garment shell and directed toward the first end; and a pair of elastic strap members, each strap member having a forward end portion and a rearward end portion with a hook patch attached to each of the forward and rearward end portions, the hook patches comprising a hook material and being releasably engageable with the first and second attachment pads.

3. The garment of claim 2, wherein each of the first and second attachment pads is attached to the garment shell with a plurality of parallel lines of adhesive.

4. The garment of claim 3, wherein each first attachment pad is attached to the garment shell with parallel lines of adhesive that are perpendicular to the longitudinal axis of such first attachment pad.

5. The garment of claim 2, wherein each of the first attachment pads has a length of at least about 9 centimeters.

6. The garment of claim 2, wherein each of the second attachment pads has a surface area of at least about 6.25 square centimeters.

7. The garment of claim 2, wherein the attachment between the hook patches and the first attachment pads has a total peel force resistance of at least about 150 grams and a total shear resistance of at least about 2000 grams.

8. A garment comprising: a garment shell having opposite inner and outer surfaces, opposite first and second ends, longitudinal sides extending between the first and second ends, corners at the intersections of the ends and the sides, a first waist section adjacent the first end, a second waist section adjacent the second end, and a crotch section between the first and second waist sections, the garment shell defining a longitudinal axis and a transverse axis;

a pair of first attachment pads attached to the outer surface in the first waist section and comprising a loop material, each of the first attachment pads having a longitudinal axis directed generally toward the nearest corner of the garment shell and forming an angle of from 25 to 45 degrees with the transverse axis of the garment shell, and each of the first attachment pads having a loop tip orientation that is directed toward the first end and is perpendicular to the longitudinal axis of the first attachment pad;

a pair of second attachment pads attached to the outer surface in the second waist section and comprising a loop material, each of the second attachment pads having a longitudinal axis directed generally toward the nearest corner of the garment shell and forming an angle of from 15 to 45 degrees with the transverse axis of the garment shell, and each of the second attachment pads having a loop tip orientation that is directed toward the second end and is perpendicular to the longitudinal axis of the second attachment pad; and a pair of strap members, each strap member having a forward end portion and a rearward end portion with a fastener comprising a hook material attached to each of the forward and rearward end portions, the fasteners being releasably engageable with the first and second attachment pads.

9. The garment of claim 8, wherein:

each first attachment pad is attached to the first waist section with a plurality of parallel lines of adhesive, the parallel lines of adhesive being perpendicular to the longitudinal axis of the first attachment pad; and each second attachment pad is attached to the second waist section with a plurality of parallel lines of adhesive, the parallel lines of adhesive being perpendicular to the longitudinal axis of the second attachment pad.

* * * * *